United States Patent
Phull et al.

(10) Patent No.: US 8,461,388 B2
(45) Date of Patent: Jun. 11, 2013

(54) PROCESS FOR THE SYNTHESIS OF PROPARGYLATED AMINOINDAN DERIVATIVES

(75) Inventors: Manjinder Singh Phull, Maharashtra (IN); Dharmaraj Ramachandra Rao, Maharashtra (IN); Rajendra Narayanrao Kankan, Maharashtra (IN)

(73) Assignee: CIPLA Limited, Mumbai (IN)

( * ) Notice: Subject to any disclaimer, the term of this patent is extended or adjusted under 35 U.S.C. 154(b) by 411 days.

(21) Appl. No.: 12/810,300

(22) PCT Filed: Dec. 19, 2008

(86) PCT No.: PCT/GB2008/004239
§ 371 (c)(1),
(2), (4) Date: Sep. 3, 2010

(87) PCT Pub. No.: WO2009/081148
PCT Pub. Date: Jul. 2, 2009

(65) Prior Publication Data
US 2011/0054218 A1     Mar. 3, 2011

(30) Foreign Application Priority Data
Dec. 24, 2007   (IN) .......................... 2539/MUM/2007

(51) Int. Cl.
*C07B 57/00*     (2006.01)
(52) U.S. Cl.
USPC ....................................................... 564/304
(58) Field of Classification Search
None
See application file for complete search history.

(56) References Cited

U.S. PATENT DOCUMENTS

| 3,123,642 A | 3/1964 | Temple et al. |
| 3,513,244 A | 5/1970 | Gittos et al. |
| 5,532,415 A | 7/1996 | Youdim et al. |

FOREIGN PATENT DOCUMENTS

| EP | 0436492 A2 | 7/1991 |
| EP | 0812190 B1 | 12/2004 |
| GB | 1003686 | 9/1965 |
| GB | 1037014 | 7/1966 |
| WO | 2009081148 A1 | 7/2009 |

OTHER PUBLICATIONS

Bonneh-Barkay, Dafna, et al., "Characterization of the neuroprotective activity of rasagiline in cerebellar granule cells," Neuropharmacology, 2005, vol. 48, pp. 406-416, Science Direct, Elsevier Ltd.
Foreign communication from the priority application—International Search Report and Written Opinion, PCT GB2008/004239, Apr. 8, 2009, 9 pages.
Foreign communication from the priority application—International Preliminary Report on Patentability, PCT/GB2008/004239, Jun. 29, 2010, 7 pages.

*Primary Examiner* — Susanne Moore
*Assistant Examiner* — Jennifer C Sawyer
(74) *Attorney, Agent, or Firm* — Conley Rose, P.C.; Rodney B. Carroll

(57) ABSTRACT

A process for preparing a compound of formula (V) or its enantiomer, which comprises:
  (a) reacting racemic aminoindan of formula (II) or its enantiomer with allylhalide in presence of a base and an organic solvent at a temperature ranging from 25 C to the reflux temperature of the solvent to give compound of formula (III);

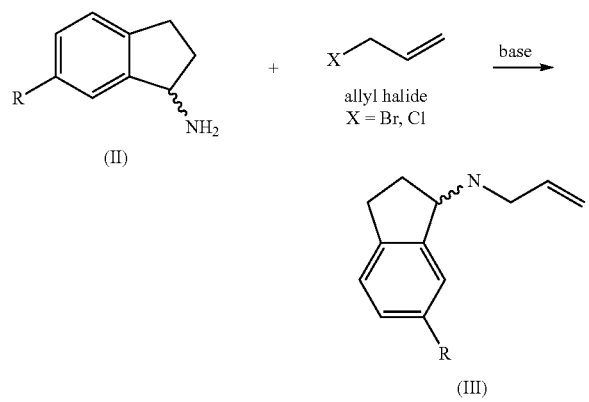

Where R is
H or

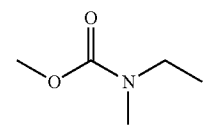

(b) reacting the compound (III) with halogenating agent in a suitable organic solvent to give a dihalo compound of formula (IV).

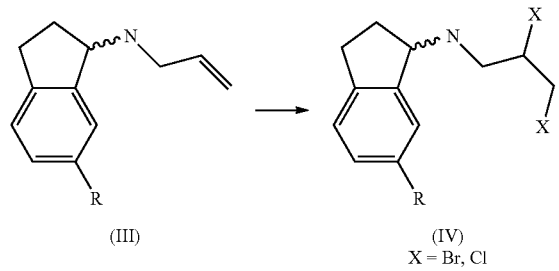

(c) treating the dihalo compound (IV) with a suitable base to give compound (V).

15 Claims, No Drawings

PROCESS FOR THE SYNTHESIS OF PROPARGYLATED AMINOINDAN DERIVATIVES

CROSS-REFERENCE TO RELATED APPLICATIONS

This application is a filing under 35 U.S.C. 371 of International Application No. PCT/GB2008/004239 filed Dec. 19, 2008, entitled "Process for the Synthesis of Propargylated Aminoindan Derivatives," claiming priority of Indian Patent Application No. 2539/MUM/2007 filed Dec. 24, 2007, which applications are incorporated by reference herein in their entirety.

FIELD OF THE INVENTION

The present invention relates to an improved and industrially safe process for the synthesis of propargylated aminoindan derivatives. More particularly, it relates to (1R)-N-prop-2-ynyl-2,3-dihydro-1H-inden-1-amine.

BACKGROUND OF THE INVENTION (1R)-N-prop-2-ynyl-2,3-dihydro-1H-inden-1-amine (I) also termed as Rasagiline or (R)N-propargyl 1-indanamine is an irreversible inhibitor of monoamine oxidase used as a monotherapy in early Parkinson's disease or as an adjunct therapy in more advanced cases.

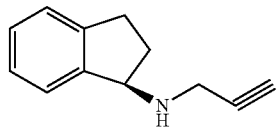

(I)

Racemic propargyl-1-aminoindan hydrochloride was described in GB1003686, GB1037014, U.S. Pat. No. 3,513,244. In the prior art the racemic mixture of propargyl-1-aminoindane was prepared by reacting 1-chloroindane or 1-bromoindane with propargylamine.

The R-enantiomer of rasagiline was described in EP0436492 and EP0812190 and the process disclosed comprises reacting optically active R-enantiomer of 1-aminoindan with propargyl bromide or propargyl chloride in presence of an organic or inorganic base and optionally in the presence of a solvent.

U.S. Pat. No. 5,532,415 discloses rasagiline R(+)-N-propargyl-1-aminoindan, its preparation, and various pharmaceutically acceptable salts thereof. U.S. Pat. No. 5,532,415 discloses that an enantiomerically pure aminoindan derivatives may be obtained by optical resolution of racemic mixtures of R- and S-enantiomers of propargyl aminoindan derivatives. Such a resolution can be accomplished by any conventional resolution method well known to a person skilled in the art. For example, the resolution may be carried out by preparative chromatography on a chiral column.

U.S. Pat. No. 5,532,415 further describes how an enantiomerically pure propargyl aminoindan can also be prepared directly from the optically active R-enantiomer of 1-aminoindan by reaction with propargyl bromide or propargyl chloride or a propargyl sulfonate ester in the presence of an organic or inorganic base, like triethylamine, pyridine, alkali metal carbonates, and bicarbonates and optionally in the presence of a suitable solvent chosen from, e.g., toluene, methylene chloride, and acetonitrile.

The process for preparation and separation of aminoindan derivatives described in the prior art have their shortcomings. Chromatography is difficult to scale up because of the large quantities of solvents used, which are difficult to dispose of. It is very difficult to carry out distillation of the high boiling aminoindan derivatives. Further use of propargyl chloride or bromide is a very difficult because it is highly toxic flammable liquid. It is decomposed explosively with shock and heat hence is not suitable for an industrial scale up.

The aim of the present invention is to provide an alternative and improved process which helps to overcome the shortcomings associated with the prior art processes.

SUMMARY OF THE INVENTION

It is an object of the present invention to provide an improved process for the synthesis of propargylated aminoindan derivatives and their salts.

It is another object of the present invention to provide an industrially safe process for the preparation of rasagiline or its salts, which excludes the use of toxic reagents.

DETAILED DESCRIPTION OF THE INVENTION

The above objects are achieved in accordance with various aspects of the present invention.

According to one aspect, the present invention provides a process which comprises reacting racemic aminoindan of formula (II) or its enantiomer with an allyl halide preferably allybromide in presence of a base and an organic solvent, preferably at a temperature ranging from 25° C. to the reflux temperature of the solvent, to give compound of formula (III). The compound of formula (III) may be optionally isolated as an acid addition salt preferably an organic acid like succinic acid, methanesulphonic acid, tartaric acid, benzoic acid, most preferably oxalic acid.

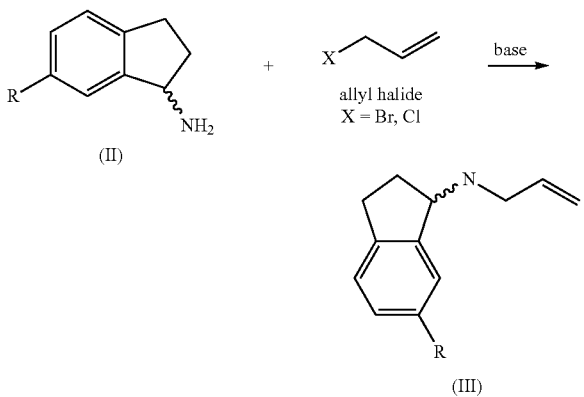

Where R is
H or

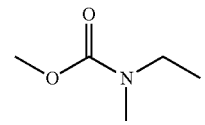

The invention also provides compounds of formulas (III) and (IV), which are new compounds.

The base is preferably an alkali metal hydroxide or carbonate, most preferably potassium carbonate. The organic solvent is preferably a $C_1$ to $C_4$ alcohol, especially isopropyl alcohol, tetrahydrofuran or acetonitrile. The preferred solvent is acetonitrile.

Compound (III) is further reacted with a halogenating reagent, preferably bromine, in a suitable organic solvent to give a dihalo compound of formula (IV).

The halogenation may be carried out with a halogen other than bromine, if desired.

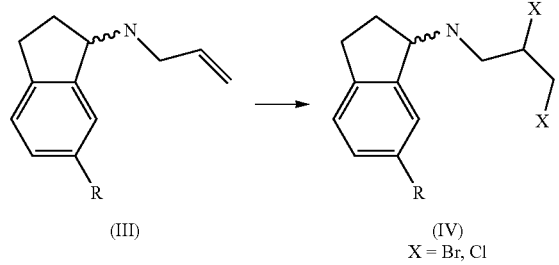

(III)                (IV)
                     X = Br, Cl

The solvent is preferably toluene, xylene, dioxan or dichloromethane, most preferably dichloromethane.

The dihalo compound (IV) is treated with a suitable base, like alkali or alkaline earth metal hydroxide or alkoxide, to give compound (V).

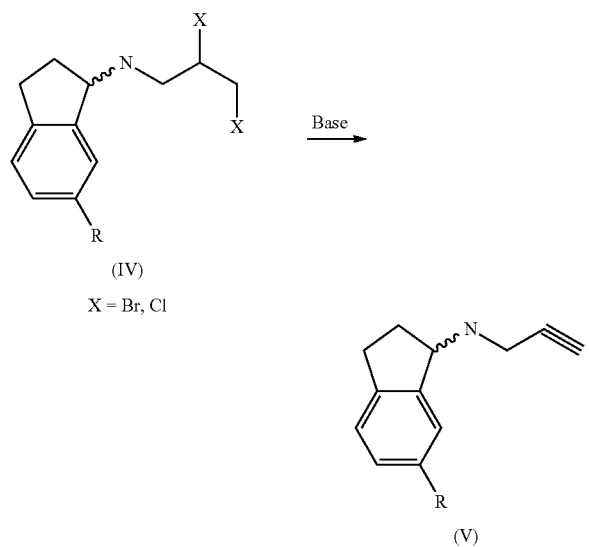

(IV)
X = Br, Cl (V)

The base used to treat the dibromo compound (IV) is preferably an alkali or alkaline earth metal hydroxide, preferably potassium hydroxide. This reaction is preferably carried out in the presence of a solvent selected from $C_1$ to $C_4$ alcohol or a $C_1$ to $C_4$ alcohol-water mixture. The $C_1$ to $C_4$ alcohol is preferably isopropyl alcohol. The compound of formula (V) may be converted to a pharmaceutically acceptable salt.

In each of the above three reactions an enantiomer of the compounds (II), (III) or (IV) may be employed instead of the racemate, especially the R-enantiomer.

According to another aspect of the present invention, there is provided an improved and safe synthesis of (R)N-propargyl 1-indanamine (I) which comprises reacting (R) 1-aminoindan with allyl bromide using a base, preferably an alkali metal hydroxide or carbonate, most preferably potassium carbonate, in presence of an organic solvent, preferably at a temperature ranging from 25° C. to the reflux temperature of the solvent used, to give a R-(−)N-allyl-1-aminoindan which can be optionally isolated as an organic acid addition acid salt preferably oxalate salt. The organic solvent is preferably a $C_1$ to $C_4$ alcohol, especially isopropyl alcohol, tetrahydrofuran or acetonitrile. The preferred solvent is acetonitrile. Allyl chloride may be used as an alternative to allyl bromide.

R-(−)N-allyl-1-aminoindan is further reacted with bromine or chlorine in a suitable organic solvent, to get R-(−)N-(2,3-dibromo propyl)-1-aminoindan. The solvent is preferably toluene, xylene, dioxan or dichloromethane, most preferably dichloromethane.

The R-(−)N-(2,3-dibromo propyl)-1-aminoindan is then heated in a suitable solvent presence of base to give (R)-N-propargyl 1-indanamine (I) which can be converted to its salts. The base is preferably an alkali or alkaline earth metal hydroxide, preferably potassium hydroxide. The solvent is preferably selected from $C_1$ to $C_4$ alcohol or a $C_1$ to $C_4$ alcohol-water mixture. The $C_1$ to $C_4$ alcohol is preferably isopropyl alcohol. The compound of formula (V) may be converted to a pharmaceutically acceptable salt.

This aspect of the invention is presented in the scheme below.

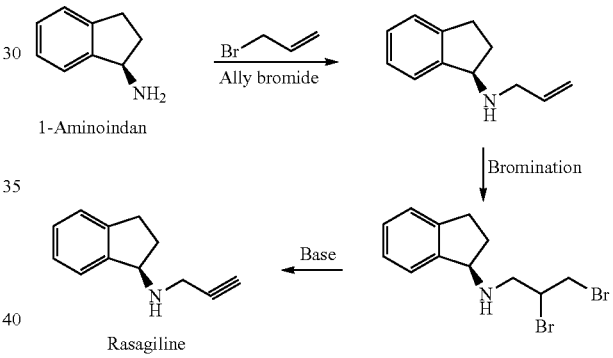

1-Aminoindan

Rasagiline

In another aspect, (R)N-propargyl 1-indanamine can be prepared by resolution of the racemic N-propargyl 1-indanamine prepared by the process of the present invention using a suitable resolving agent, preferably L-tartaric acid. Typically, in this aspect of the present invention (R)N-propargyl 1-indanamine (I) is prepared by the process as described above, more particularly by reacting 1-aminoindan with allyl bromide using a base preferably potassium carbonate in presence of an organic solvent preferably acetonitrile at a temperature ranging from 25° C. to the reflux temperature of the solvent used, to give N-allyl-1-aminoindan which can be optionally isolated as an organic acid addition acid salt preferably oxalate salt. N-allyl-1-aminoindan is further reacted with bromine in a suitable organic solvent preferably dichloromethane to get N-(2,3-dibromo propyl)-1-aminoindan which is then heated in a suitable solvent presence of base to give racemic N-propargyl 1-indanamine, which is resolved using a suitable resolving agent preferably L-tartaric acid to give (R)N-propargyl 1-indanamine which can be converted to its pharmaceutically acceptable salts.

In another aspect, the present invention provides a process for the resolution of the racemic intermediates (III) and (IV) using a chiral resolving agent selected from the corresponding chiral acid of tartaric acid, dipara toluoyl tartaric acid, camphorsulphonic acid, mandelic acid and the like.

Another aspect of the present invention is to provide an alternate process for the synthesis of rasagiline which comprises reacting 1-aminoindan with halo acetone to get compound of formula (VI) which is brominated to give dibromo intermediate of formula (VII) which when further treated with base give rasagiline as depicted in the scheme below.

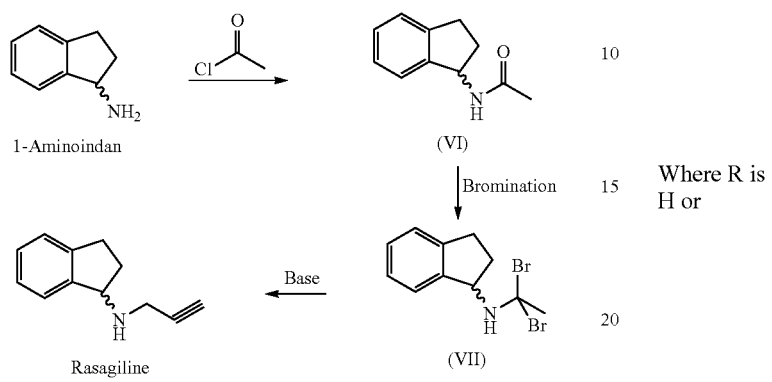

Resolution of the intermediate of formula (VI and VII) using a chiral resolving agent selected from the corresponding chiral acid of tartaric acid, dipara toluoyl tartaric acid, camphorsulphonic acid, mandelic acid and the like and further converting it to the corresponding enantiomer of rasagiline forms another aspect of the present invention.

In yet another aspect, the present invention provides an improved process for the synthesis of N-ethyl-N-methylcarbamic acid 3(R)-(2-propylamino)-2,3-dihydro-1H-inden-5-yl ester L-tartrate (I) which comprises following the process as given in scheme below.

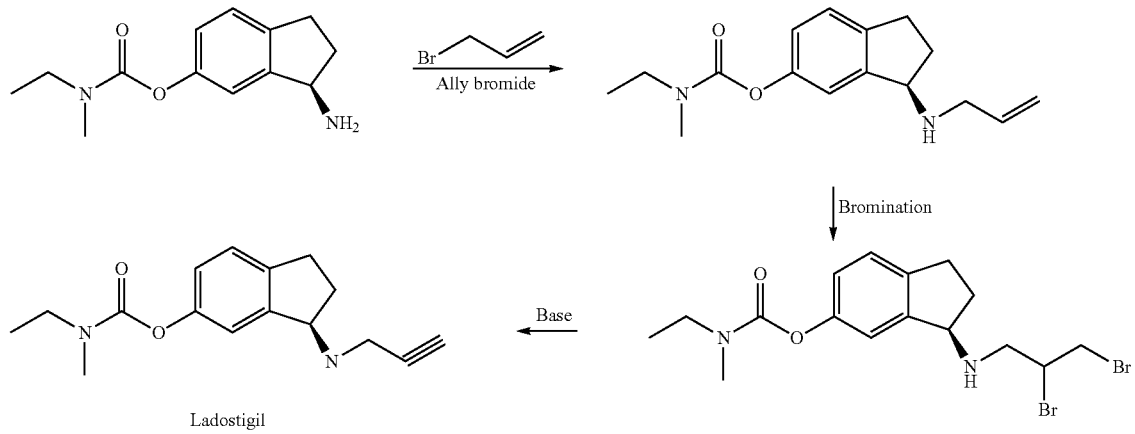

According to another aspect of the invention, there is provided a process for preparing a compound of formula (III) by reacting a compound of formula (II) with an allyl bromide or other allyl halide, in accordance with the following scheme.

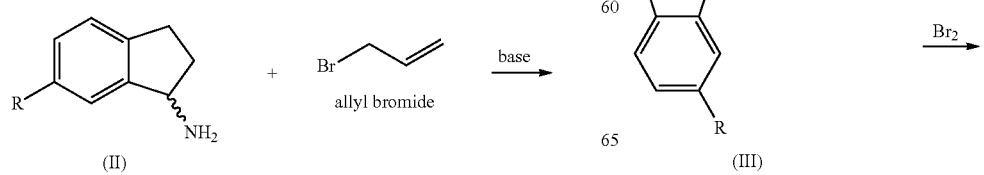

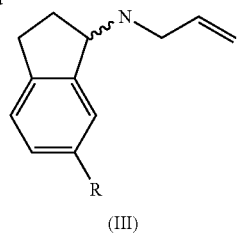

Where R is
H or (structure of N-ethyl-N-methylcarbamate shown)

According to another aspect of the invention, there is provided a process for preparing a compound of formula (IV) by reacting a compound of formula (III) with a bromine or other halogen, in accordance with the following scheme.

-continued

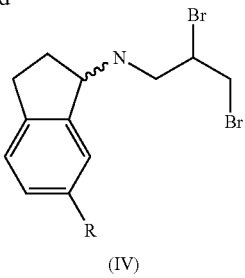

According to another aspect of the invention, there is provided a process for preparing a compound of formula (V) by treating a compound of formula (IV) with a suitable base, in accordance with the following scheme.

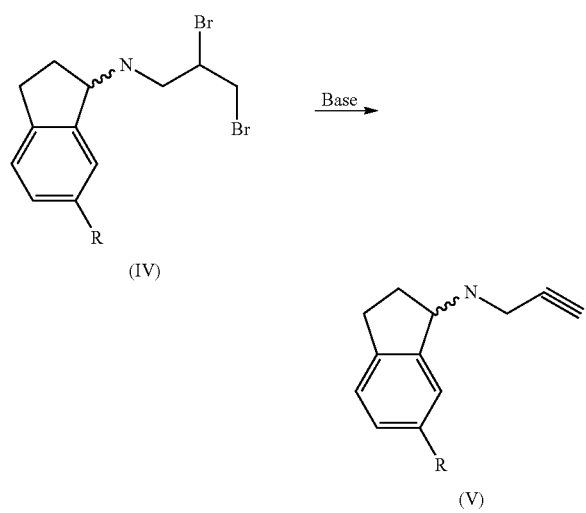

In each of the above three reactions, an enantiomer of the compounds (II), (III) or (IV) may be employed instead of the racemate, especially the R-enantiomer. The conditions for the reactions are preferable the same as described above.

EXAMPLES

This invention will be better understood by the following examples. However, the examples illustrate, but do not limit the scope of the invention. Those skilled in the filed of the art will readily appreciate that the specific methods and results discussed are merely illustrative of the invention as described more in the claims that follow thereafter.

Example 1

To the stirred solution of (R)-1-aminoindan (100 gm) in 1000 ml of acetonitrile was added 100 gm of potassium carbonate. The resulting suspension was stirred at 60° C. to 70° C. Allyl bromide (60 gm) was added dropwise to the reaction mass at 60-70° C. The reaction mass stirred was further stirred at reflux temp for about 12-13 hrs. The reaction mass was then quenched in 2.5 lit of water and later extracted with 500 ml of ethyl acetate. The organic phase was dried over sodium sulphate. 125 gm of oxalic acid was added to the ethyl acetate layer at 25-30° C. The resulting precipitate was at 25-30° C. for 2 hrs & filtered. The solid was recrystallized from methanol to yield 100 gm of R(−)N-allyl-1-aminoindan oxalate.

Example 2

R-(−)N-allyl-1-aminoindan oxalate salt (100 gm) was suspended in 1000 ml of dichloromethane, 500 ml of 10% NaOH solution was added to the suspension slowly. The organic layer was washed with water and dried over sodium sulphate & concentrated under vacuum to about 500 ml. To the organic phase was added bromine (60 gm dissolved in 250 ml of dichloromethane) at 0-5° C. dropwise After completion of addition the reaction mass was stirred at 25-30° C. for about 1 hr. The reaction mass was quenched into 2.5 lit water. Organic phase was separated and washed with 250 ml 10% NaOH solution, the organic phase was dried over sodium sulphate and concentrated to residue to yield (115 gm) of R-(−)N-(2,3dibromo propyl)-1-aminoindan.

Example 3

R-(−)N-(2,3dibromo propyl)-1-aminoindan (115 gm) was dissolved in 500 ml denatured industrial spirit, 100 ml water was added followed by 100 gm potassium hydroxide. The mixture was heated to 80-90 C for 5 hrs. The reaction mass was quenched into 2.5 lit water and extracted with 250 ml ethyl acetate three times. The combined organic phase was dried over sodium sulphate and concentrated to about 500 ml. 100 gm oxalic acid was added to the ethyl acetate concentrate under stirring at 25-30° C. and stirred for 1 hr. The resulting precipitated was isolated by filtration to yield 50 gm of (R)-N-propargyl 1-indanamine oxalate.

Example 4

1-aminoindan (100 gm) was stirred in 1000 ml of acetonitrile 100 gm of potassium carbonate was added and was stirred at 60° C. to 70° C. Allyl bromide (60 gm) was added slowly to the reaction mass at 60-70° C. The reaction mass was refluxed for about 12-13 hrs. The reaction mass was then quenched in 2.5 lit of water and later extracted with 500 ml of ethyl acetate. The organic phase was dried over sodium sulphate. 125 gm of oxalic acid was added to the ethyl acetate layer at 25-30° C. The resulting precipitate was at 25-30° C. for 2 hrs and filtered. The solid was recrystallized from methanol to yield 100 gm of the N-allyl-1-aminoindan oxalate.

Example 5

N-allyl-1-aminoindan oxalate salt (100 gm) was suspended in 1000 ml of dichloromethane, 500 ml of 10% NaOH solution was added to the suspension slowly. The organic layer was washed with water and dried over sodium sulphate and concentrated under vacuum to about 500 ml. To the organic phase was added bromine (60 gm dissolved in 250 ml of dichloromethane) at 0-5° C. dropwise After completion of addition the reaction mass was stirred at 25-30° C. for about 1 hr. The reaction mass was quenched into 2.5 lit water. Organic phase was separated and washed with 250 ml 10% NaOH solution, the organic phase was dried over sodium sulphate and concentrated to residue to yield (115 gm) N-(2, 3dibromo propyl)-1-aminoindan.

Example 6

N-(2,3dibromo propyl)-1-aminoindan (100 gms) was dissolved in isopropyl alcohol (200 ml) at 25-30C. L-tartaric acid (20 gm) dissolved in (250 ml) of water was added at 25-30 C and the reaction mass was heated at 60° C. for 30 min. and cooled to 25-30 C under stiffing. The resulting suspension was filtered. This solid was refluxed under stirring in a mixture of methanol:isopropyl alcohol 1:1 (500 ml). The slurry was cooled at 0-5° C. and filtered to give R-(−)N-(2,3dibromo propyl)-1-aminoindan as a tartrate salt.

Example 7

N-allyl-1-aminoindan (10 gms) was dissolved in isopropyl alcohol (50 ml) at 25-30 C. L-tartaric acid (3.6 gm) dissolved in (5.5 ml) of water was added at 25-30 C and the reaction mass was heated at 60° C. for 30 min. and cooled to 25-30 C under stirring. The resulting suspension was filtered. This solid was refluxed under stirring in a mixture of methanol:isopropyl alcohol 1:1 (50 ml). The slurry was cooled at 0-5° C. and filtered to give R-(−)N-allyl-1-aminoindan tartrate.

Example 8

N-(2,3dibromo propyl)-1-aminoindan (115 gm) was dissolved in 500 ml denatured industrial spirit, 100 ml water was added followed by 100 gm potassium hydroxide. The mixture was heated to 80-90 C for 5 hrs. The reaction mass was quenched into 2.5 lit water and extracted with 250 ml ethyl acetate. The organic phase was dried & concentrated to residue. The residue was dissolved in isopropyl alcohol (160 ml) at 25-30 C. L-tartaric acid (13.5 gm) dissolved in (20 ml) of water was added at 25-30 C and the reaction mass was heated at 60° C. for 30 min. and cooled to 25-30 C under stirring. The resulting suspension was filtered. This solid was refluxed under stiffing in a mixture of methanol:isopropyl alcohol 1:1 (300 ml). The slurry was cooled at 0-5° C. and filtered. This solid was further stirred with 10% sodium hydroxide solution and extracted with dichloro methane 250 ml. The organic layer was separated, dried and concentrated under vacuum to residue. The residue is dissolved in isopropyl alcohol and 5.7 ml methane sulphonic acid was added dropwise at 25-30 C. The resulting suspension was cooled to 0-5° C. and filtered. The solid was further recrystallised from isopropyl alcohol to get 10 gms (R)N-propargyl 1-indanamine mesylate HPLC (99.8%) Chiral purity (99.5%).

The invention claimed is:

1. A process for preparing N-propargyl 1-indanamine or its enantiomer, which comprises:
    (a) reacting racemic 1-aminoindan or its enantiomer with an allyhalide in presence of a base to give N-allyl-1-aminoindan or its enantiomer;
    (b) halogenating the N-allyl-1-aminoindan or its enantiomer with a halogenating agent in a suitable organic solvent to give N-(2,3 dihalo propyl)-1-aminoindan or its enantiomer; and
    (c) treating the N-(2,3-dihalo propyl)-1-aminoindan or its enantiomer with a suitable base to give N-propargyl 1-indanamine or its enantiomer.

2. The process according to claim 1, wherein the base used in step (a) is an alkali metal carbonate.

3. The process according to claim 1, wherein the base used in step (a) is potassium carbonate.

4. The process according to claim 1, wherein the organic solvent used in step (a) is a $C_1$ to $C_4$ alcohol, tetrahydrofuran or acetonitrile.

5. The process according to claim 1, wherein the organic solvent used in step (b) is toluene, xylene, dioxan or dichloromethane.

6. The process according to claim 1, wherein the base used in step (c) is an alkali or alkaline earth metal hydroxide or alkoxide.

7. The process according to claim 1, wherein the base used in step (c) is potassium hydroxide.

8. The process according to claim 1, wherein step (c) is carried out in the presence of a solvent selected from $C_1$ to $C_4$ alcohol or a $C_1$ to $C_4$ alcohol-water mixture.

9. The process according to claim 1, wherein the allyl halide is allyl bromide.

10. The process according to claim 1, wherein the halogen used in step (b) is bromine.

11. The process according to claim 1, wherein step (a) is carried out at a temperature from 25° C. up to the reflux temperature of the solvent used in step (a).

12. The process according to claim 1, wherein the N-allyl-1-aminoindan is formed as an acid addition salt thereof.

13. The process according to claim 1, wherein the 1-aminoindan is the R-enantiomer thereof.

14. The process according to claim 1, wherein the 1-aminoindan is the racemate, and further comprising treating the racemic N-propargyl 1-indanamine produced in step (c) with a suitable resolving agent to produce (R)-N-propargyl 1-indanamine.

15. The process according to claim 14, wherein the resolving agent is L-tartaric acid.

* * * * *

UNITED STATES PATENT AND TRADEMARK OFFICE
CERTIFICATE OF CORRECTION

PATENT NO.       : 8,461,388 B2                      Page 1 of 1
APPLICATION NO. : 12/810300
DATED            : June 11, 2013
INVENTOR(S)      : Phull et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 482 days.

Signed and Sealed this

Eighth Day of September, 2015

Michelle K. Lee
*Director of the United States Patent and Trademark Office*